United States Patent [19]

Rigaud

[11] Patent Number: 4,473,354

[45] Date of Patent: Sep. 25, 1984

[54] PROCESS AND EQUIPMENT DESIGNED FOR THE STANDARD PREPARATION OF TEETH BEFORE INSTALLING A CROWN

[76] Inventor: Michel Rigaud, 3 Chemin du Pensionnat, 69350 La Mulatiere (Rhone), France

[21] Appl. No.: 256,882

[22] Filed: Apr. 24, 1981

[30] Foreign Application Priority Data

Apr. 25, 1980 [FR] France .................................. 80 09922

[51] Int. Cl.³ .............................................. A61C 5/08
[52] U.S. Cl. .................................................. 433/218
[58] Field of Search ................. 433/218, 219, 165, 166

[56] References Cited

U.S. PATENT DOCUMENTS

| 749,624 | 1/1904 | McCullough | 433/165 |
|---|---|---|---|
| 2,723,455 | 11/1955 | Oberley | 433/166 |
| 2,735,181 | 2/1956 | Carpenter | 433/166 |
| 2,855,673 | 10/1958 | Gruenwald | 433/166 |
| 4,158,256 | 6/1979 | Wiland et al. | 433/219 |
| 4,264,307 | 4/1981 | Neuwirth | 433/166 |

FOREIGN PATENT DOCUMENTS 2012268 10/1971 Fed. Rep. of Germany ...... 433/166

Primary Examiner—John J. Wilson
Attorney, Agent, or Firm—Remy J. VanOphem

[57] ABSTRACT

A groove is cut on the lateral surfaces of the tooth, at an equal distance from the gum to the sealed base of the tooth. A diaboloshaped drill is then used to shape the occlusal mass above the groove and the cervical mass below the groove. When shaping the cervical groove, a lower horizontal path is also defined which is used as a guide for the finishing drill. The rough spherical shape of the tooth is thus transformed into a roughly straight tapered trunk onto which the prosthetic crown is installed.

15 Claims, 28 Drawing Figures

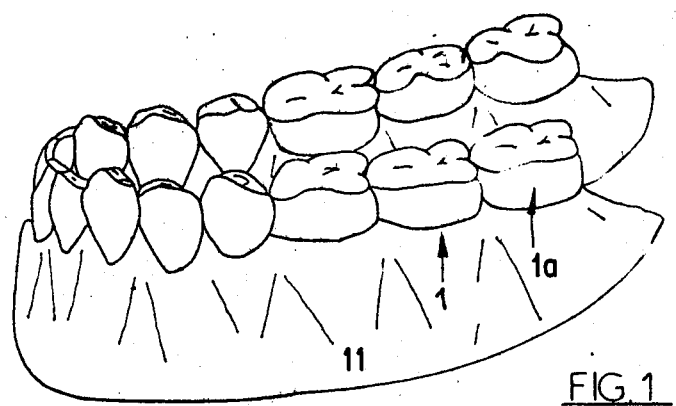
FIG. 1
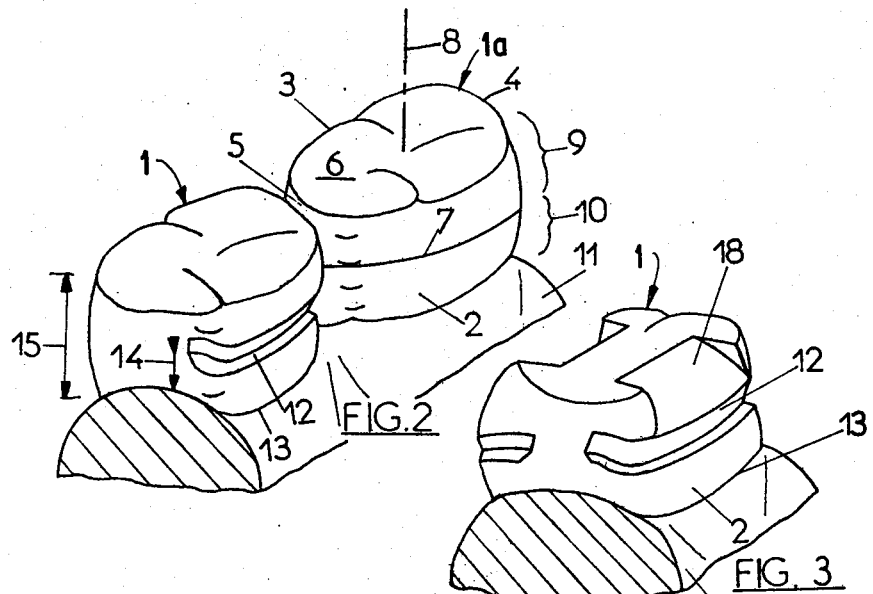
FIG. 2
FIG. 3
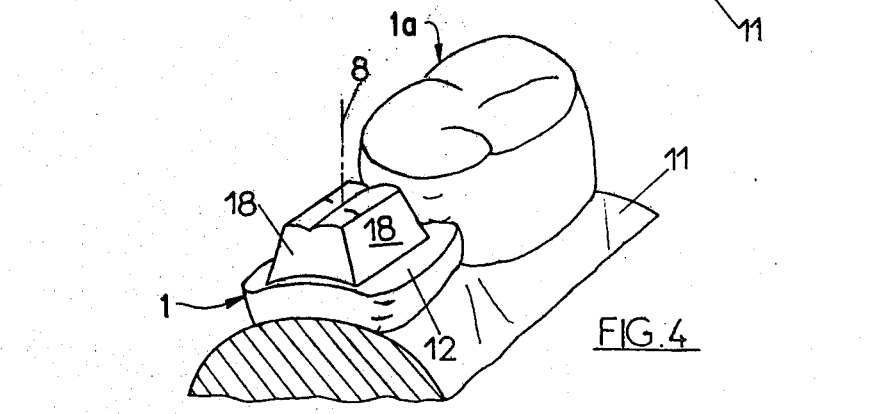
FIG. 4

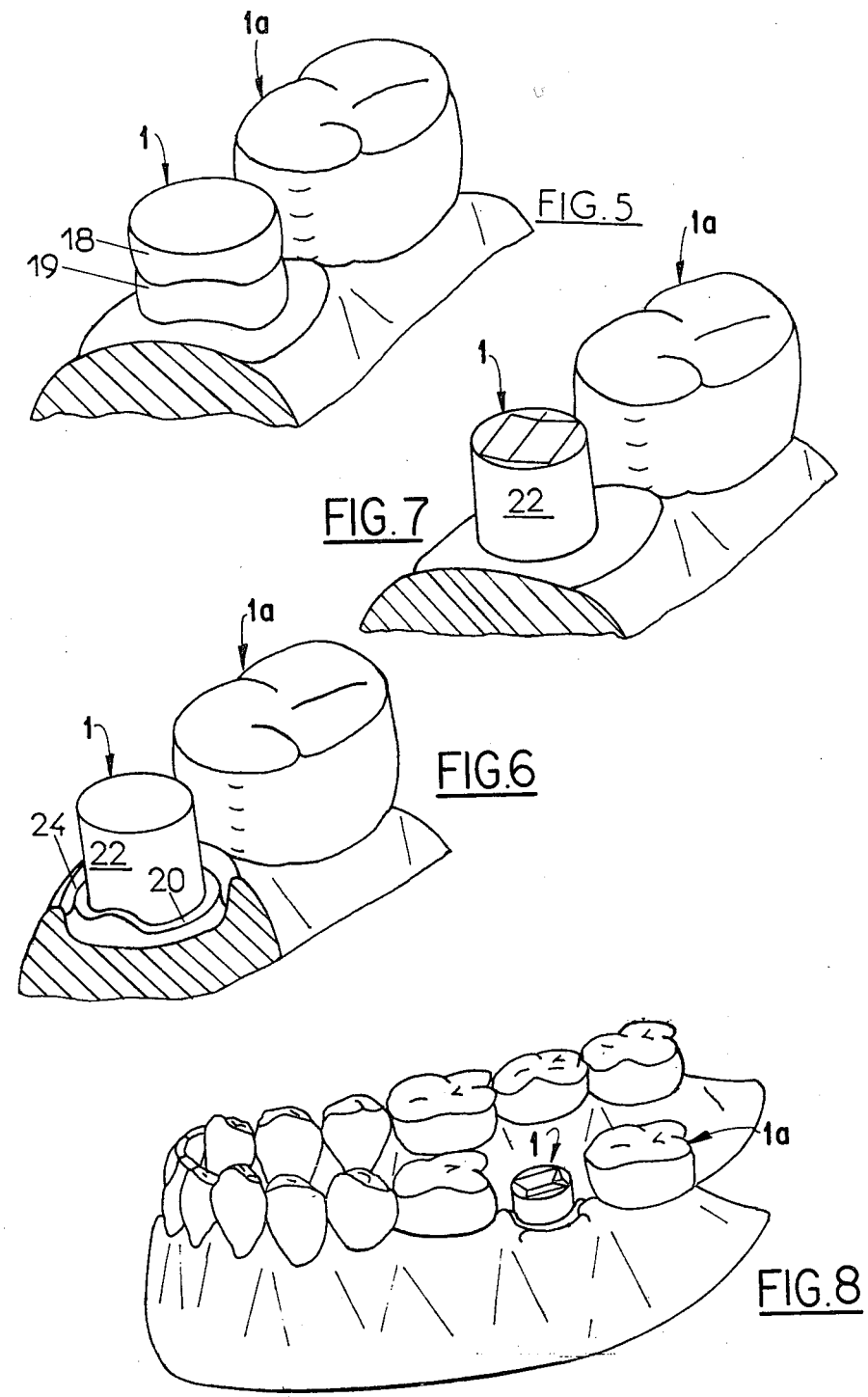

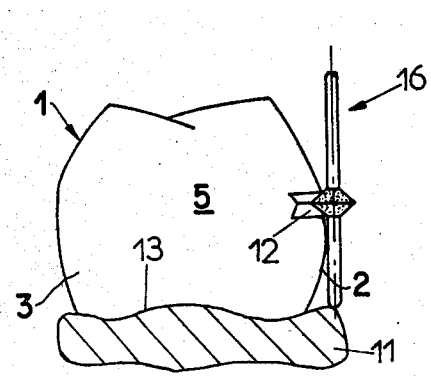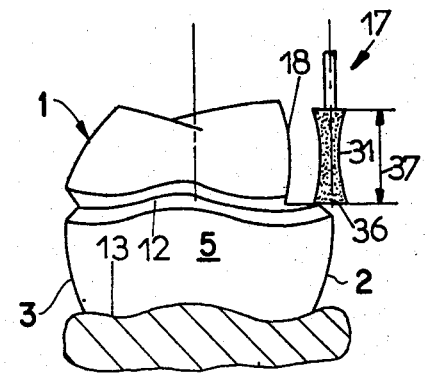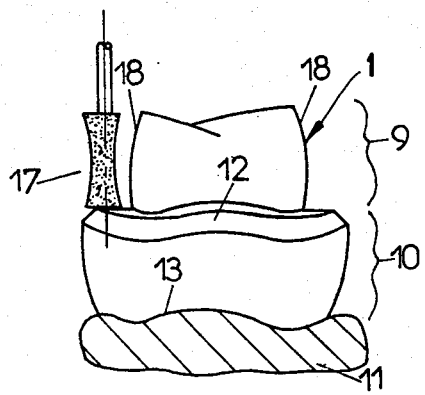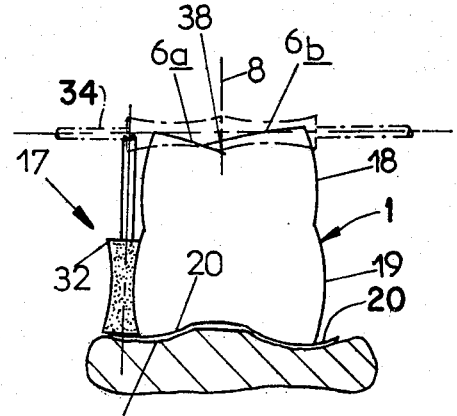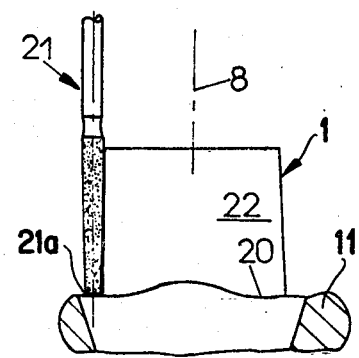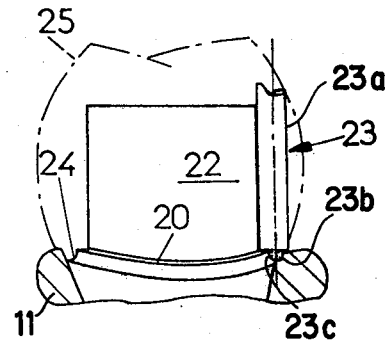

PROCESS AND EQUIPMENT DESIGNED FOR THE STANDARD PREPARATION OF TEETH BEFORE INSTALLING A CROWN

BACKGROUND OF THE PRESENT INVENTION

The present invention pertains to the process and equipment required for the cutting of the teeth prior to the installation of prosthetic crowns.

Usually, the preparation required before the installation of a crown on a tooth may be interpreted as consisting of the transformation of a spherical mass which is amputated at its base and at the top of a spherical portion, the base being sealed on a plane and the top remaining free, into a roughly straight tapered trunk whose large base coincides with the sealed base of the mass disposed thereabove.

Actually, in order to restore a tooth using a prosthetic crown, the approximately spherical mass of the tooth has to be transformed into an approximately straight tapered trunk. Thus, part of the peripheral dental surface is eliminated so as to be subsequently replaced by a restoring material.

The work involved on the approximately spherical mass, in order to change it into an approximately tapered trunk, leads to the definition of four vertical surfaces on the tooth. These surfaces are defined by the anatomical location of this organ within its environment, namely the buccal cavity, and by a free horizontal surface.

Each one of the four vertical surfaces is actually part of an approximately spherical surface of the approximately spherical mass. These four vertical surfaces of the approximately spherical mass are: the vestibular surface facing the cheek, the lingual or palatal surface facing the tongue, the distal surface facing the posterior tooth of the dental arch that includes the tooth considered, and the mesial surface facing the anterior tooth of the dental arch that includes the tooth considered.

Assuming that these four vertical surfaces each theoretically define a plane, the four respective planes so defined may be each considered to be parallel with the tooth axis. The tooth axis itself roughly defines the inserting axis of the future prosthetic crown.

Furthermore, the tooth includes an occlusal surface, which is the upper surface of the tooth. The occlusal surface is a free, horizontal surface defining a plane which is approximately perpendicular with the tooth axis.

A lower horizontal, sealed surface, representing the base of the rough spherical mass, is located at the junction between the portion of the tooth penetrating the gum with the bone supporting that tooth.

A line, traced along the approximately spherical mass and running at mid-height across the vestibular, lingual, distal and mesial surfaces, defines an intermediate plane which is approximately perpendicular with the tooth axis. The molar and premolar teeth are convex on all of their surfaces. The twelve teeth which belong to the incisivo-canine group are partially concave on their lingual surfaces, in the case of the lower teeth, and on their palatal face, in the case of the upper teeth. The intermediate plane thus defined divides the tooth into two anatomical zones.

The occlusal mass is located above the intermediate plane, and includes the occlusal surface of the approximately spherical mass. The cervical, or gingival mass is located below the intermediate plane, and includes the lower horizontal sealed surface of the approximately spherical mass. Together, the occlusal and cervical masses define the coronary mass which is an approximately spherical mass whose median axis is vertical.

The metal-type restoration techniques used by the contemporary crowns require strict specifications for the convergence of the sides and the limits of the peripheral cuts.

Despite the required accuracy, it is necessary to work by hand, using rotary-type tools, so as to perform the transformation into the approximately straight tapered trunk onto which the metal restoration of the dental organ has to fit with a minimum of friction. Actually, the mass to be transformed is not accessible to spinning or lathe-type machine tools. The tools that are used consist of drills in which a drill body is rigidly mounted with a handle which is rotatably driven by any suitable means. The machining processes currently used which include the cutting of the tooth without any preliminary rough shaping, do not guarantee the success of the operation as to the taper, and as to the location of the lower limit of the cut.

SUMMARY OF THE PRESENT INVENTION

The present invention, using a more reliable method and more reliable apparatus, is directed to the elimination of these disadvantages.

Using the method and apparatus of the present invention, the sequence of operations on the tooth should be performed according to a process defined by the morphology of the coronary mass. The selection of the specific tools used depends on the proportions of the coronary mass, particularly in the vertical direction.

The method of the present invention for the cutting of a tooth before installing a prosthetic crown is characterized by the following operations.

A groove is cut in the tooth, equidistant with the sealed base of the tooth. The occlusal mass is then re-shaped above the groove, using a rough shaping drill. The cervical mass is then reshaped below the groove, using the rough shaping drill, so as to obtain a lower peripheral guiding path. Next, the sides of the coronary mass are ground, using a drill whose stop piece is guided by contracting the guiding path. Finally, a chamfer is provided along the free edge of the guiding path, using a drill in which one stop piece is in contact with the guiding path, and whose other circular stop piece comes in contact with the surfaces machined during the previous operation.

According to another variation of the method of the invention, the complete shaping of the tooth includes the complete sequence of the first five above described operations on the vesticular and lingual sides, as well as two rough shaping operations, which do not use the machined groove, followed by the last two above mentioned operations on the mesial and distal surfaces.

According to still another variation of the method of the present invention, all of the the above described operations apply to the four lingual, vestibular, distal and mesial surfaces of the tooth.

The drill, according to the present invention, used during the first operation described above includes a drill body with a mobile lateral surface mounted at the end of a handle. The mobile lateral surface is, rigidly mounted in alignment with the handle and with a straight stop piece disposed remote from the handle. The straight stop piece is rounded at one end and is approximately equal in length to half of the distance separating the occlusal and lower horizontal sealed surfaces of the coronary mass of the tooth considered.

The drill according to the present invention, which is used during the second and third operations described above, is approximately shaped as a diabolo. It includes a mobile lateral surface and at least one outwardly extending edge at each end of the mobile lateral surface.

The drill according to the present invention, which is used during the fourth operation described above, includes a slightly tapered lateral mobile surface. The end having the larger cross-section is rigidly mounted at the end of a handle, and the end whose cross-section is the smallest represents a smooth stop piece.

The drill according to the present invention, which is used during the last operation, includes at one end of a handle a smooth, cylindrical contact surface which engages the lateral tapered surface of the tooth and an annular flat contact surface which engages the guiding path provided on the tooth and, in the center of the annular flat contact surface, a mobile portion is provided which can be embossed, concave, or convex or which may have a straight generatrix.

The attached, schematic drawing and detailed description, offered by way of example and not by way of limitation, will give a better understanding of the present invention.

BRIEF DESCRIPTION OF THE DRAWINGS

In the drawing:

FIG. 1 is an elevational view of a lower jaw including a preselected tooth which should be provided with a prosthetic crown;

FIGS. 2 through 7 are partial elevational views of the jaw of FIG. 1, and illustrate the consecutive operations on the preselected tooth according to the method of the present invention;

FIG. 8 is an elevation of the lower jaw of FIG. 1 after the preselected tooth has been machined according to the method of the present invention;

FIGS. 23 through 28 are lateral views illustrating, on a tooth being shaped, the various operations involved in the invented process.

DETAILED DESCRIPTION OF THE PREFERRED EMBODIMENTS

Figures 9, 10, 11, 12, 12A:
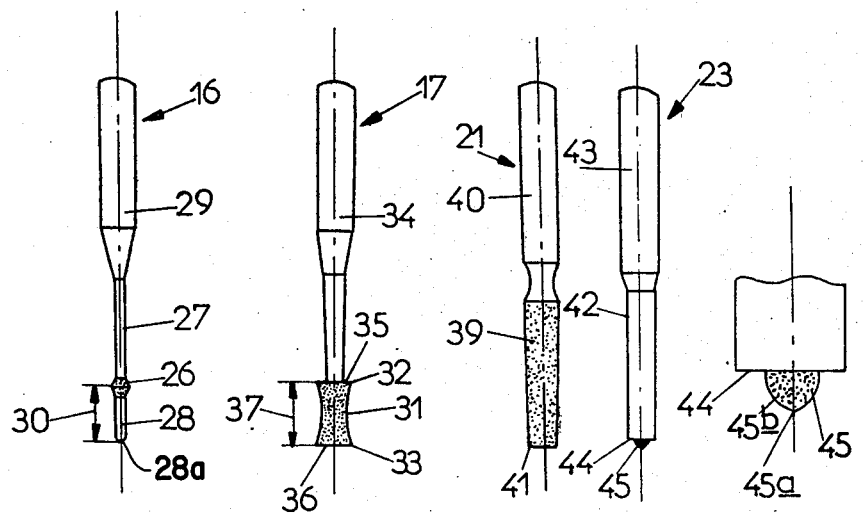
FIGS. 9 through 22 are lateral views of the various types of drills according to the present invention which are used to carry out the method of the present invention.

FIG. 1 illustrates a jaw in which a preselected tooth 1 needs to be shaped prior to the installation of prosthetic crown. In the example illustrated, the preselected tooth 1 is a molar. In order to clarify this description, the following terminology shall apply to the various parts of a tooth.

As shown in FIG. 2, with reference to an arbitrary tooth, each tooth 1a includes a vestibular surface 2 which faces the cheek, a lingual or palatal surface 3 which faces the tongue, a distal surface 4 which faces the posterior tooth of the dental arch containing the tooth 1a, and a mesial surface 5 which faces the anterior tooth of the dental arch containing the arbitrary tooth 1a considered. These surfaces represent the four "vertical" surfaces of the tooth 1a. Actually, in the case of the molar and premolar teeth, these four "vertical" surfaces are convex and the total or coronary mass of the tooth 1a may be compared with an approximately spherical mass from which a spherical portion has been removed at the base and at the top.

An occlusal surface 6 represents the upper surface of the tooth 1a.

An imaginary line 7 is considered around the larger perimeter of the coronary mass. The imaginary line 7 is located approximately halfway between the upper and lower ends of the spherical portions which have theoretically been removed from the approximately spherical mass of the tooth 1a. The imaginary line 7 defines an intermediate plane which is roughly perpendicular with the axis 8 of the tooth 1a. Furthermore, the imaginary line 7 and the intermediate plane divide the coronary mass into two anatomical areas. An occlusal mass 9 is defined above the intermediate plane. A gingival or cervical mass 10 is defined below the intermediate plane and faces the gum 11.

As indicated above, the method of the present invention pertains to the shaping of a preselected tooth 1 and involves the transformation of an aproximately spherical mass into a straight tapered trunk which will allow for the installation of a prosthetic crown, so as to eventually restore a complete tooth.

The method of the present invention includes as steps the following consecutive operations:

(a) The first operation is shaping of a guiding groove as shown in FIGS. 2 and 23.

During this operation, a linear groove 12 is cut along the vestibular surface 2 and the lingual surface 3 of the preselected tooth 1. The linear groove 12 is located at a constant predetermined distance 14 from a sealed base 13 of the approximately spherical mass of the preselected tooth 1. The constant predetermined distance 14 does not exceed one half of the height 15 separating the lower and upper ends of the approximately spherical mass. Therefore, a drill 16 is used, as shown in FIG. 23, which is automatically guided by and supported on the edge of the gum 11 adjacent the sealed base 13 of the cervical mass of the preselected tooth 1.

When sufficient intervals are provided between the preselected tooth 1 and the teeth adjacent thereto, the same operation may be performed on the distal and mesial surfaces 4 and 5 of preselected tooth 1.

(b) The second operation is the machining of the occlusal mass 9 as illustrated in FIGS. 3 and 24.

The occlusal mass defined above linear groove 12 is methodically shaped using a rough shaping drill 17, shown in FIG. 24. This machining operation is performed along the whole perimeter of the preselected tooth 1, including on the distal surface 4 and on the mesial surface 5, even if the linear groove 12 could not be provided on these surfaces due to the close proximity of the adjacent teeth. Thus, a first new peripheral surface 18 is created on the occlusal mass 9, as shown in FIG. 25.

(c) The third operation includes the machining of the cervical mass 10, as shown in FIGS. 5 and 26.

The same rough shaping drill 17 is used to shape the cervical mass 10 located below the linear groove 12, as was used to shape the occlusal mass 9. The third operation creates a second new peripheral surface 19 along the whole perimeter of the preselected tooth 1. While roughly shaping the sides of the preselected tooth 1, a peripheral horizontal guiding path 20 should also be shaped. The third operation may be accurately performed by using a drill, such as the rough shaping drill 17, of appropriate height, due to the presence of the linear groove 12 which is located at a constant distance from the gums or from the cervical base of the preselected tooth 1.

(d) The fourth operation involves resurfacing the sides, as shown in FIGS. 6 and 27.

Using a drill 21 guided along the peripheral horizontal guiding path 20, the finishing or surfacing operation of the first and second new peripheral surfaces 18 and 19 of the preselected tooth 1 may be performed, as best shown in FIG. 27. During this fourth operation, the rough surfaces, that is, the first and second new peripheral surfaces 18 and 19, should be eliminated. A straight, tapered trunk 22 is thus obtained which is flared in the opposite direction of the drill 21, but whose taper has the same absolute value as that of the drill 21, whose axial end 21a is stopped by the peripheral horizontal guiding path 20.

(e) The fifth operation is the chamfering of the base of the preselected tooth 1, as depicted in FIGS. 7 and 28.

Using a drill 23 which includes a lateral contact surface 23a which comes in contact with the tapered trunk 22, and a transverse surface 23c which comes in contact with the peripheral horizontal guiding path 20, the chamfer 24 best shown in FIG. 28, is obtained. The drill 23 is provided with a cane tip 23b which provides a smooth chamfer 24 whose height and width are constant along the perimeter of the preselected tooth 1. In the course of this fifth operation, the edge of the gum 11 is pushed to the outside or slightly curetted. Such a rotating curettage is known to be desirable by those skilled in the art. The gum 11 shall eventually be able to recover its normal position around the lower thinned edge of the prosthetic crown 25.

FIG. 8 illustrates a jaw in which the preselected tooth 1 is already cut, as indicated above, to receive the crown 25.

The remainder of the present description concerns the various types of drills designed for the implementation of the method of the present invention.

The drill 16 used to perform the first operation is represented on FIG. 9 and includes a drill body 26 with a lateral mobile surface located between two smooth cylindrical contact surfaces 27 and 28, which are coaxial with a handle 29. The two smooth cylindrical contact surfaces 27 and 28 may have the same diameter. The smooth cylindrical contact surface 27 spreads from the handle's axial end to the drill body 26, whereas the free end 28a of surface 28 may be round. The distance 30 separating the free end 28a from the middle of the drill body 26 does not exceed one half of the total height of the approximately spherical mass of the preselected tooth 1 to be machined.

The drill body 26 may be designed in various manners. The drawing illustrates a drill body including two parts which are symmetrical on either side of a plane which includes the middle of the drill body. The two parts that have a concave generatrix are separated from one another by an edge, but this arrangement is only exemplary and it would be possible to design a drill with a asymmetrical body, without any edge, and whose generatrix could be concave, convex, broken line type or any other way.

When using the drill 16, the free end 28a should slightly contact the edge of the gum 11, along the line where the peripheral horizontal guiding path 20 will eventually be cut. Usually, this line represents the junction between the preselected tooth 1 and the gum 11, and the drill body 26 cuts the linear groove 12 at midheight, as shown in FIG. 23. Therefore, all points of linear groove 12 are equidistant to the line defined by the gum 11 along the preselected tooth 1. In the event that it would not be possible to cut the linear groove 12 along the entire perimeter of the preselected tooth 1, due to the presence of the adjacent teeth, the cutting operation is performed in such a way that the vestibular and lingual portions of the linear groove 12 mesially and distally stop above the taper of the preselected tooth 1 at its junction with the gum 11.

The drill 17 used for the second and third operations, and illustrated in FIG. 10, includes a diabolo shaped body having a handle 34 and a groove 31 has a concave generatrix located between two edges 32 and 33. The edge 32, which is located adjacent the handle 34 of the drill 17, is adjacent to an annular surface 35 which may be abrasive as is the groove 31. The annular end surface 36 which is located adjacent the edge 33, however, may be a smooth surface.

In order to use the drill 17 during the second operation, its annular end surface 36 should be placed in contact with the surface of the linear groove 12 as shown in FIG. 24. The distance 37 separating the two edges 32 and 33 is approximately equal to one half of the overall height of the roughly spherical mass of the tooth. The machining operation is performed by keeping the axis of the drill 17 approximately parallel with the axis of the future prosthetic crown or in slight convergence with that axis. The active generatrix of the groove 31 must remain generally with the ligament supporting the roughly spherical mass of the tooth in the occlusal portion. The machining depth of the first new peripheral surface 18 thus obtained is equal to the diameter of the drill body of the drill 17, as measured at the edges 32 and 33, or to that of the linear groove 12.

The drill 17 may also be used for the machining of the occlusal surface 6 of the tooth as depicted in FIG. 26. In this case, the mesio-distally orientated median path 38 of the occlusal surface 6 of the preselected tooth 1 is used as a guiding groove. The drill handle 34 is then parallel with the half of the occlusal surface 6 being machined. Therefore, during the machining operation performed on the lingual half 6a of the occlusal surface 6, the drill handle 34 is lingually orientated, whereas the drill body is vestibularly orientated. During the machining of the vestibular half 6b of the occlusal surface, the drill handle 34 is vestibularly orientated, and the drill body is lingually orientated. In both cases, the annular end surface 36 of the drill 17 is placed in the median path 38 for the machining of horizontal grooves, while selecting either the diameter of the edges 32 and/or 33 (the diameter of these edges may differ) or the diameter of the groove 31 as a reference for the machining depth. The machined grooves meet, following a horizontal translation and the morphology of the occlusal slopes and domes of the occlusal surface 6. It is thus possible to obtain, without any prior rough shaping operation, the finishing of the occlusal surface 6 at a desired depth.

The preliminary machining of the occlusal mass improves the visibility of the cervical mass 10, and provides a better access to the cervical mass. This is particularly important with respect to the line of junction between the gum 11 and the preselected tooth 1. Indeed, special attention should be given so as not to needlessly injure the gum 11, and so as to achieve the most accurate positioning of the junction and finishing line of the future prosthetic crown 25.

In order to perform the machining operation on the vestibular, cervical side, the axis of the drill 17 should be parallel with the insertion axis of the future crown, this axis being in alignment with the general tooth axis 8, shown in FIGS. 5 and 26. During the third operation, the edge 32 of the drill body is placed inside the linear groove 12 which has been machined in the course of the first operation. The drill 17 is deeply engaged into each end portion of the machined path, using a horizontal motion of variable amplitude. While maintaining the axis of the drill 17 in the same direction and guiding the drill along the linear groove 12, a translation motion enables the machined paths to meet around the perimeter of the preselected tooth 1. The third operation thus completes the rough shaping of the lower portion of the straight tapered trunk, while providing the peripheral horizontal guiding path 20 of adequate depth, at a preselected height and generally in a plane which is perpendicular to the tooth axis 8. The entire third operation is performed without any injury to the gum 11, using the same method on the four sides of the preselected tooth.

The drill 21, used to perform the fourth operation and illustrated in FIG. 11, includes a slightly tapered lateral active surface 39 whose larger end is rigidly mounted with a handle 40, and whose free end is of smaller diameter and represents a smooth transversal contact surface 41. The transversal contact surface 41 may be concave or convex and should have the same shape as the annular end surface 36 of the drill 17.

In order to operate with the drill 21, the transversal contact surface 41 is placed in contact with the peripheral horizontal guiding path 20, as depicted in FIG. 27, the axis of the drill 21 remaining parallel with the tooth axis 8. A circular motion of the drill 21, while in contact with the peripheral horizontal guiding path 20, allows for the surfacing of a tapered surface, using the abrasive surface of the drill 21. The taper of the surface thus obtained is equal to that of the abrasive surface of the drill 21.

A dome shaped contact surface for the transversal contact surface 41 reduces the friction and is therefore more desirable in order to prevent any overheating.

The drill 23 used to perform the fifth operation is illustrated in FIG. 12 and has several elements starting from the axial end of the handle 42. These elements include a smooth cylindrical contact surface 43, a flat annular smooth contact surface 44, and an abrasive dome shaped portion 45, sometimes called a cane tip or a flat annular smooth contact lever handle, the abrasive dome shaped portion 45 being located at the center of the flat annular smooth contact surface 44. The flat annular smooth contact surface 44 may include a sharp or round end 45a as depicted in FIG. 12a, and a generatrix 45b which may be convex, concave, straight or broken.

When operating, the axis of the drill 23 is kept parallel with the tooth axis 8, the cylindrical contact surface 43 is kept in contact with the tapered surface of the tapered trunk 22 which has been previously machined on the preselected tooth 1, and the flat annular smooth contact surface 44 is kept in contact with the peripheral horizontal guiding path 20 of the tooth, as shown in FIG. 28. With the drill 23, it is possible to obtain the chamfer 24 whose direction, height and width remain constant, and which could not be obtained through prior art methods.

FIGS. 13 through 22 and FIG. 22a illustrate various types of drills designed to the specifications of several variations of the present invention. These drills may be used in lieu of the above described drills to perform the first, second and third operations.

Figures 13, 14, 15, 16, 17:
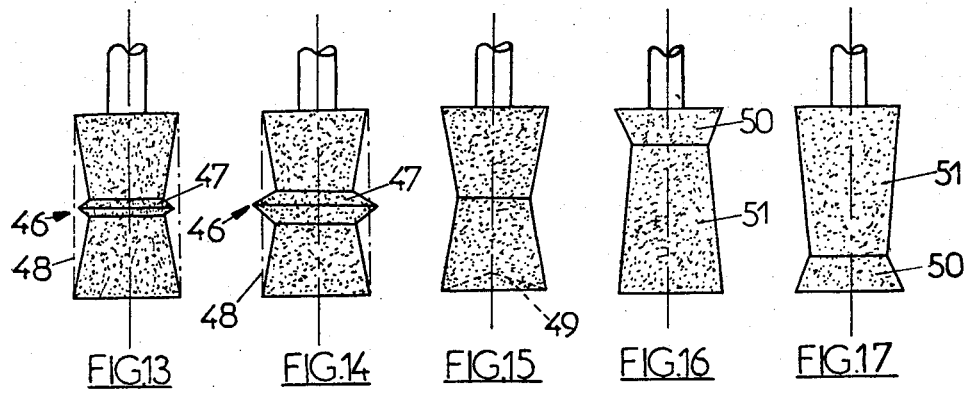

The active surfaces of the drill illustrated in FIG. 13 are diabolo shaped and include an annular flange 46 with an edge 47 in its plane of symmetry. The annular flange 46 is located at mid-height on the surfaces considered. The edge 47 is included within the imaginary cylinder 48 drawn from the axial ends of the drill body. FIG. 14 illustrates a similar drill in which the edge 47 is located outside of the cylinder 48. In both cases, the annular flange 46 includes two surfaces whose generatrix may either be straight, convex or concave.

The drill illustrated in FIG. 15 includes a diabolo shaped body with a concave tapered surface 49 at its free end.

The drill illustrated in FIG. 16 includes an asymmetrical, diabolo shaped body consisting of a relatively short but significantly tapered abrasive surface 50 on the side of the handle, and of a relatively long and slightly tapered abrasive surface 51 at the free end of the drill. The body of the drill illustrated in FIG. 17 is also shaped as an asymmetrical diabolo, but the directions of the surfaces 50 and 51 are oppositely disposed with reference to the previous ones.

Figures 18, 19, 20, 21, 22, 22A:
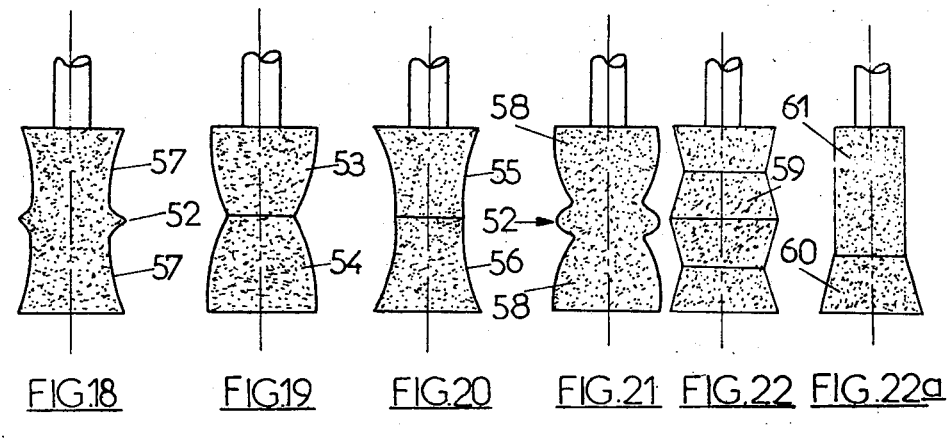

The drill illustrated in FIG. 18 includes a diabolo shaped body with an annular flange located at mid-height, like the drills illustrated in FIGS. 13 and 14. The end surfaces 57 of the drill body are concave, and since all of the generatrix of the drill body are curved, no edge is provided on the flange 52.

The drill illustrated in FIG. 19 includes a diabolo shaped body whose two abrasive surfaces 53 and 54 have a convex generatrix.

The drill illustrated in FIG. 20 still includes a diabolo shaped body, but has two abrasive surfaces 55 and 56 with a concave generatrix.

The drill illustrated in FIG. 21 is similar to that of FIG. 18, since it also includes a diabolo shaped body with an annular flange 52 on which no edge is provided. But while the generatrix of the end surfaces 57 of the drill body illustrated in FIG. 18 are concave, the end surfaces 58 of the drill body illustrated in FIG. 21 are convex.

The drill illustrated in FIG. 22 includes a drill body including four abrasive surfaces that are tapered with straight generatrix and which define together a double diabolo with one central cutting edge 59.

The drill illustrated in FIG. 22a includes only one edge and only one flared surface 60, as well as a cylindrical portion 61.

The present invention would still apply to other modified versions of these drills derived from the following shapes.

The drills may include a lateral, abrasive surface with two main areas, flared in opposite directions, and on which an annular flange may be provided at the junction of these two main areas.

Diabolo shaped drills may be provided with two edges at the end, the diameter of one being longer than that of the other.

Diabolo shaped drills may be used including two areas which are flared in opposite directions and located on either side of a central, cylindrical area.

These and other variations and modifications from the detailed description above are offered, by way of example, and not by way of limitation, and are included within the intended scope of the claims appended hereto.

What is claimed as novel is as follows:

1. A method of reshaping a tooth and preparing said tooth for the installation of a prosthetic crown wherein said tooth has a vertical longitudinal axis, a sealed base adjacent to gums, a natural vertical peripheral surface including a vertical lingual surface, a vertical distal surface, a vertical vestibular surface and a vertical mesial surface, a horizontal occlusal surface, an occlusal mass and a cervical mass, said method comprising the consecutive steps of:

cutting an approximately horizontal groove in a portion of said natural vertical peripheral surface using first drill means;

removing a peripheral portion of said tooth above said approximately horizontal groove using second drill means to obtain a first new vertical peripheral surface thereabove, said second drill means comprising first stop means cooperating with said approximately horizontal groove so as to guide said second drill means; and removing a peripheral portion of said tooth below said approximately horizontal groove using third drill means to obtain a second new vertical peripheral surface therebelow, said third drill means comprising second stop means cooperating with said approximately horizontal groove so as to guide said third drill means.

2. The method of claim 1 wherein said approximately horizontal groove comprises:

a first horizontal groove portion cut into said vertical lingual surface; and a second horizontal groove portion cut into said vertical vestibular surface.

3. The method of claim 1 wherein said approximately horizontal groove is cut into said tooth at approximately the midpoint between said occlusal mass and said cervical mass.

4. The method of claim 1 wherein said approximately horizontal groove is located at a first predetermined constant distance above said sealed base of said tooth, and wherein said first drill means comprises third stop means cooperating with said gums to guide said first drill means and a third tooth machining means spaced said first predetermined distance from said third stop means.

5. The method of claim 4 wherein said first predetermined distance does not exceed one-half of the height of said tooth.

6. The method of claim 4 wherein said third drill means comprises a second tooth machining means extending a second predetermind distance from said third stop means, said second predetermined distance being less than said first predetermined distance so that said third drill means simultaneously produces said second new vertical peripheral surface and a horizontal guide surface therebelow, said horizontal guide surface being spaced a constant third predetermined distance above said sealed base.

7. The method of claim 6 further comprising, after said two removing steps, the step of finishing said first and second new vertical peripheral surfaces using fourth drill means comprising:

a fourth stop means cooperating with said horizontal guide surface to guide said fourth drill means; and a third tooth machining means extending a fourth predetermined distance from said fourth stop means, said fourth predetermined distance being no less than the difference between the height of said tooth and said third predetermined distance so that said first and second new vertical peripheral surfaces are machined to produce a single straight third new vertical peripheral surface.

8. The method of claim 7 further comprising, after said finishing step, the step of chamfering said portion of said tooth below said horizontal guide surface using a fifth drill means comprising a fifth stop means cooperating with said third new vertical peripheral surface to guide said fifth drill means, sixth stop means cooperating with an inner portion of said horizontal guide surface to guide said fifth drill means and a fourth tooth machining means extending from said horizontal drill means adjacent to said sixth stop means, said fourth tooth machining means removing an outer portion of said horizontal guide surface.

9. The method of claim 1 further comprising after said two removing steps, the step of finishing said first and second new vertical peripheral surfaces using fourth drill means so that said first and second new vertical peripheral surfaces are machined to produce a single straight third new vertical peripheral surface.

10. The method of claim 9 wherein said third drill means produces a horizontal guide surface in the tooth adjacent the gums and further wherein said fourth drill means further comprises fourth stop means cooperating with said horizontal guide surface to guide said fourth drill means.

11. The method of claim 10 wherein said fourth drill means is tapered towards said fourth stop means so that said third new vertical peripheral surface is flared in the opposite direction of said fourth drill means.

12. The method of claim 1 wherein said third drill means comprises a second tooth machining means extending a predetermined distance from said third stop means, said predetermined distance being less that the minimum height of said horizontal groove from said sealed base so that said third drill means simultaneously produces said second new vertical peripheral surface and a horizontal guide surface therebelow, said horizontal guide surface being spaced a constant third predetermined distance above said sealed base.

13. The method of claim 12 further comprising, after said two removing steps, the step of chamfering said portion of said tooth below said horizontal guide surface using a fifth drill means comprising a fifth stop means cooperating with said second new vertical peripheral surface to guide said fifth drill means, a sixth stop means cooperating with an inner portion of said horizontal guide surface to guide said fifth drill means and fourth tooth machining means extending from said fifth drill means adjacent to said sixth stop means for removing an outer portion of said horizontal guide surface.

14. The method of claim 13 wherein said fifth drill means comprises a drill bit wherein said fifth stop means comprises an approximately cylindrical longitudinal trunk, said fourth machining means comprises a machining portion extending longitudinally from one end of said approximately cylindrical longitudinal trunk, and said sixth stop means comprises a flat annular shoulder on said end of said approximately cylindrical longitudinal trunk disposed around said machining portion.

15. The method of claim 14 wherein said machining portion is hemispherical in shape.

* * * * *

UNITED STATES PATENT AND TRADEMARK OFFICE
CERTIFICATE OF CORRECTION

PATENT NO. : 4,473,354
DATED : September 25, 1984
INVENTOR(S) : Michel Rigaud

It is certified that error appears in the above-identified patent and that said Letters Patent is hereby corrected as shown below:

Column 2, line 65, delete the comma ",".

Column 5, line 59, delete "a" and insert ---- an ----.

In the Claims

Column 9, line 42, delete "third" and insert ---- first ----.

Column 9, line 43, delete "fromsaid" and insert ---- from said ----.

Column 10, line 13, delete "horizontal" and insert ---- fifth ----.

Column 10, line 40, delete "thereblow" and insert ---- therebelow ----.

Signed and Sealed this

Ninth Day of April 1985

[SEAL]

Attest:

DONALD J. QUIGG

Attesting Officer  Acting Commissioner of Patents and Trademarks